US012780768B2

(12) United States Patent
Pacholik et al.

(10) Patent No.: US 12,780,768 B2
(45) Date of Patent: Nov. 3, 2026

(54) PROCESS FOR PREPARING METHANOL

(71) Applicant: Technische Universität Wien, Vienna (AT)

(72) Inventors: Gernot Pacholik, Vienna (AT); Karin Föttinger, Vöcklabruck (AT)

(73) Assignee: Technische Universität Wien, Vienna (AT)

( * ) Notice: Subject to any disclaimer, the term of this patent is extended or adjusted under 35 U.S.C. 154(b) by 650 days.

(21) Appl. No.: 18/029,583

(22) PCT Filed: Oct. 8, 2021

(86) PCT No.: PCT/AT2021/060369
§ 371 (c)(1),
(2) Date: Mar. 30, 2023

(87) PCT Pub. No.: WO2022/073055
PCT Pub. Date: Apr. 14, 2022

(65) Prior Publication Data
US 2023/0365481 A1 Nov. 16, 2023

(30) Foreign Application Priority Data
Oct. 8, 2020 (AT) .............................. A 50869/2020

(51) Int. Cl.

| | |
|---|---|
| ***C07C 29/153*** | (2006.01) |
| ***B01J 21/04*** | (2006.01) |
| ***B01J 27/051*** | (2006.01) |
| ***B01J 37/03*** | (2006.01) |
| ***B01J 37/04*** | (2006.01) |
| ***B01J 37/06*** | (2006.01) |

(Continued)

(52) U.S. Cl.
CPC ............. *C07C 29/153* (2013.01); *B01J 21/04* (2013.01); *B01J 27/051* (2013.01); *B01J 37/035* (2013.01); *B01J 37/04* (2013.01); *B01J 37/06* (2013.01); *B01J 37/088* (2013.01); *B01J 37/10* (2013.01)

(58) Field of Classification Search
CPC ........ C07C 29/153; C07C 31/04; B01J 23/34; B01J 23/04
See application file for complete search history.

(56) References Cited

U.S. PATENT DOCUMENTS

2010/0331581 A1 12/2010 Kharas et al.
2023/0234037 A1* 7/2023 Sheehan .................. B01J 27/02 518/714

FOREIGN PATENT DOCUMENTS

CN 108794298 A 11/2018
CN 109201096 A 1/2019
CN 110833843 A 2/2020

OTHER PUBLICATIONS

Huijie, Q. et al., "Nickel and manganese co-modified K/MoS2 catalyst: high performance for higher alcohols synthesis from CO hydrogenation" Catalysis Communications, vol. 4, No. 7, Jul. 1, 2003, pp. 339-342.

(Continued)

*Primary Examiner* — Jafar F Parsa
(74) *Attorney, Agent, or Firm* — Workman Nydegger

(57) ABSTRACT

A process for the production of methanol ($CH_3OH$) from carbon dioxide ($CO_2$) and hydrogen ($H_2$), wherein $CO_2$ is reacted with $H_2$ over a manganese-promoted molybdenum (IV) sulfide catalyst; as well as a catalyst for such a process and a production process for the catalyst.

9 Claims, 6 Drawing Sheets

(51) Int. Cl.
*B01J 37/08* (2006.01)
*B01J 37/10* (2006.01)

(56) References Cited

OTHER PUBLICATIONS

International Preliminary Report on Patentability received for PCT Patent Application No. PCT/AT2021/060369, mailed on Apr. 20, 2023, 15 pages (9 pages of English Translation and 6 pages of Original Document).
International Search Report and Written Opinion received for PCT Patent Application No. PCT/AT2021/060369, mailed on Jan. 20, 2022, 18 pages (8 pages of English Translation and 10 pages of Original Document).
Liu et al., "Synthesis of higher alcohols from CO2 hydrogenation over Mo—Co—K sulfide-based catalysts", Journal of the Taiwan Institute of Chemical Engineers vol. 76, 2017, pp. 18-26.
Zeng et al., "Synthesis of mixed alcohols with enhanced C3+ alcohol production by CO hydrogenation over potassium promoted molybdenum sulfide", Applied Catalysis B: Environmental, vol. 246, 2019, pp. 232-241.

* cited by examiner

PROCESS FOR PREPARING METHANOL

The present invention relates to a process for the catalytic production of methanol from carbon dioxide and hydrogen. Furthermore, the invention relates to a catalyst for the production of methanol from carbon dioxide and hydrogen. Finally, the invention relates to the use of a catalyst for the production of methanol from carbon dioxide and hydrogen.

BACKGROUND OF THE INVENTION

According to the prior art, various processes are available for the fully synthetic production of alcohols. In industrial terms, processes in which carbon monoxide (CO) or carbon dioxide ($CO_2$) serve as starting materials are of particular importance. These processes are divided into processes for the production of methanol ($CH_3OH$) on the one hand and processes for the production of higher alcohols, i.e., alcohols with more than one carbon atom, on the other hand. The selectivity and the yield of the desired alcohol are important criteria.

According to the prior art, the industrial production of methanol is effected, for example, via the hydrogenation of carbon monoxide or carbon dioxide, in each case at high pressures, using suitable catalysts. Both reactions occur during the hydrogenation starting from a synthesis gas, although the yield of $CO_2$ hydrogenation is in need of improvement.

Liu et al., Journal of the Taiwan Institute of Chemical Engineers, 76 (2017), page 18, describe the production of higher alcohols by means of $CO_2$ hydrogenation with a Mo—Co—K sulfide catalyst, wherein the catalyst may comprise $MoS_2$, among other things.

Qi et al., Catalysis Communication, 4 (2003), page 339, describe CO hydrogenation by means of K/$MoS_2$. The addition of manganese to the catalyst is described as well, with a Ni/Mn/K/$MoS_2$ catalyst finally being described as suitable for the hydrogenation of CO. The result shows a very high selectivity for alcohols with an overall yield of 81.7%. Therein, methanol accounts for 45.8% and higher alcohols account for 53.3% ($C_n$ alcohols with n=2, 3, 4 and 5).

Zeng et al., Applied Catalysis B: Environmental, 246 (2019), page 232, describe the production of higher alcohols with at least three carbon atoms ($C_n$ alcohols with n≥3) by means of CO hydrogenation over $MoS_2$ promoted with potassium.

DETAILED DESCRIPTION OF THE INVENTION

The selective processes known from the prior art for the production of methanol are often based on carbon monoxide as the starting material. Processes based on $CO_2$ either are not very selective or require expensive catalysts or, respectively, complex process conditions. If CO is to be used as a starting material, an additional reaction step is necessary for the production of CO, whereas $CO_2$ is available in practically unlimited quantities (for example, it accumulates as a waste product in the form of flue gas during the combustion of hydrocarbons).

It is the object of the present invention to provide a selective and inexpensive process and a catalyst for the selective hydrogenation of $CO_2$ to methanol. Furthermore, the catalyst should be sulfur tolerant, i.e., tolerant of trace amounts of sulfur compounds in the reaction gas.

This object is achieved by a selective process for the production of methanol ($CH_3OH$, MeOH) from carbon dioxide ($CO_2$) and hydrogen ($H_2$), wherein $CO_2$ is reacted with $H_2$ over a manganese-promoted $MoS_2$ catalyst.

The invention is based on the finding that a manganese-promoted $MoS_2$ catalyst catalyzes the $CO_2$ hydrogenation in a highly selective manner. In particular, the very high yield of methanol and the high specificity of the formation of methanol are surprising in comparison to already known sulfur-tolerant catalysts. In this process, there is almost no formation of higher alcohols, and the amount of by-products formed, such as CO or $CH_4$, is also small.

Although the exact reaction mechanism is not yet known to the inventors, a two-stage reaction sequence with an upstream RWGS step (Reverse Water-Gas Shift Reaction) and a subsequent CO hydrogenation to methanol $$CO_2+H_2 \rightarrow CO+H_2O$$

$$CO+2H_2 \rightarrow CH_3OH$$

is rather improbable, since comparative tests on the $MoS_2$ catalyst promoted with manganese have shown hardly any conversion of CO with $H_2$ to form $CH_3OH$. The high yield and selectivity is all the more surprising.

Therefore, in one aspect, the invention relates to the use of a manganese-promoted $MoS_2$ catalyst for the production of methanol from $CO_2$ and $H_2$.

The object stated at the outset is further achieved by a catalyst comprising manganese-promoted molybdenum (IV) sulfide ($MoS_2$), the manganese-promoted molybdenum (IV) sulfide having a layered structure which can have various disorders. The structure can be described by way of the borderline cases 2H—$MoS_2$ and 3R—$MoS_2$. The proportion of manganese is such that the molar ratio of Mn to Mo is 0.1 to 0.5:1, preferably 0.2 to 0.4:1. Furthermore, XPS studies have shown that manganese can exist in the oxidation states (II) and (III).

Manganese can preferably be present as Mn(II) sulfide and/or Mn(III) sulfide. In addition, manganese can also be present as Mn(II) oxide, Mn(III) oxide, Mn(II) hydroxide, Mn(III) hydroxide or MnOOH.

According to the invention, the manganese-promoted molybdenum(IV) sulfide ($MoS_2$) can be a mixed crystal of manganese sulfide(s) and $MoS_2$, with the basic structure being formed by the $MoS_2$ and manganese sulfide(s) being incorporated into this basic structure, wherein, optionally, manganese oxide(s), manganese hydroxide(s) and/or MnOOH are additionally incorporated into the basic structure according to the previous paragraph.

Additionally, the catalyst can be promoted with potassium. In this case, a phase of a K(I) salt, preferably $K_2CO_3$, is present on the surface of the manganese-promoted molybdenum(IV) sulfide. Such a catalyst is hereinafter referred to as manganese-promoted molybdenum(IV) sulfide with potassium.

The catalyst can additionally have a carrier on which the manganese-promoted molybdenum(IV) sulfide (optionally with potassium) is applied. The carrier can be a porous material. For example, the carrier can be an aluminium oxide or aluminium oxide hydroxide such as $Al_2O_3$ or AlO(OH).

The catalyst preferably consists of Mn(0.1 to 0.50)$MoS_2$, preferably Mn(0.2 to 0.4)$MoS_2$, optionally with a carrier as mentioned above.

The catalyst described above has proved to be useful for the process. Therefore, in one aspect, the invention relates to such a catalyst.

Furthermore, reaction conditions in the process have proved to be advantageous which have a pressure that has been increased in comparison to standard conditions. Therefore, it is preferably intended for the reaction to take place at a pressure of ≥10 bar. For example, the pressure can be 10 bar to 200 bar or 10 bar to 100 bar. In one embodiment variant, the pressure was between 18 bar and 23 bar.

In principle, the reaction can proceed over a wide temperature range. Suitable temperatures are, for example, between 140° C. and 320° C. If a pure manganese-promoted $MoS_2$ catalyst is used, the ideal temperature range is preferably between 170° C. and 220° C.

If a manganese-promoted $MoS_2$ catalyst mixed with potassium is used, the ideal temperature range for the reaction is somewhat higher, namely preferably between 260° C. and 300° C.

It is preferably envisaged that the partial pressure ratio of $CO_2$ to $H_2$ is about 1:2.5 to 3.5, preferably approximately 3. This means that the partial pressure of hydrogen should be about 2.5 to 3.5 times higher than the partial pressure of $CO_2$.

Furthermore, it has surprisingly been shown that the addition of an inert gas to the reaction mixture of $CO_2$ and $H_2$, for example, of a noble gas (such as, e.g., helium) or of nitrogen, hardly impedes the reaction. The yield decreased only slightly. The partial pressure of inert gas can be about 1:0.5 to 1.5—based on $CO_2$. The realization that inert gas does not interfere with the reaction means that flue gas, which contains mostly nitrogen, can also be used as a source of $CO_2$.

In one embodiment variant, the $CO_2$ can therefore come from flue gas. In this case, the process according to the invention is a selective process for the production of methanol from $CO_2$ and $H_2$, the source of $CO_2$ being flue gas, wherein $CO_2$ is reacted with $H_2$ over a manganese-promoted $MoS_2$ catalyst. Such a process is suitable for subjecting flue gas to recycling.

Although all manganese-promoted $MoS_2$ catalysts are suitable as catalysts, those presented according to the next-described process prove to be particularly efficient. Therefore, in one aspect, the invention relates to a process for the production of a manganese-promoted $MoS_2$ catalyst for the production of methanol from $CO_2$ and $H_2$, comprising the steps of:

(i) forming a mixture of water, ammonium molybdate (particularly $(NH_4)_6Mo_7O_{24}.4H_2O$), thiourea ($CH_4N_2S$) and a water-soluble manganese(II) salt;

(ii) raising the temperature of this mixture in an autoclave to 150-250° C. and increasing the pressure to such a level that part of the water remains liquid, maintaining the temperature and pressure until the thiourea decomposes and a sulfide mixture comprising manganese sulfide and $MoS_2$ forms;

(iii) washing the sulfide mixture obtained from step (ii);

(iv) drying the washed sulfide mixture from step (iii);

(v) calcining the dried and washed sulfide mixture from step (iv) under inert gas to obtain the manganese-promoted $MoS_2$ catalyst.

The sulfide mixture in step (ii) and in subsequent steps may comprise Mn(II) oxide, Mn(III) oxide, Mn(II) hydroxide, Mn(III) hydroxide or MnOOH. In addition, these compounds form, in particular, at the upper end of the temperature range.

The pressure in the autoclave preferably ranges from 5 to 40 bar, preferably it is about 15.5 bar.

Optionally, potassium can also be added to the washed sulfide mixture before it is calcined, but after it has been dried. The addition of potassium can take place in the form of an aqueous K(I) solution, e.g., a $K_2CO_3$ solution, wherein a drying step is then provided before the calcination. The K(I) solution can be added via ultrasonic dispersion.

Furthermore, a carrier can be provided for the catalyst. In this case, the sulfide mixture is mixed with a carrier prior to the calcination step. The carrier can be a porous material. Aluminium oxides, e.g., AlO(OH) or $AlO_2O_3$, have proved to be suitable carriers.

Preferably, the carrier is precipitated, preferably from a precursor compound, while raising the temperature of the mixture in the autoclave to 150-250° C. and increasing the pressure to such a level that part of the water remains liquid. The precursor can be $Al(NO_3)_3$, for example, and initially it is present in a dissolved state. Subsequently, the dissolved precursor can be precipitated as $Al(OH)_3$ or AlO(OH).

DETAILED DESCRIPTION OF THE INVENTION

Further advantages and details of the invention are shown in the accompanying figures and are explained in further detail in the following description.

The reaction conditions in the examples shown in the figures at the beginning of the reaction, the way how the gas mixture is passed over the catalyst, are summarized in Table 1.

Figure 1:
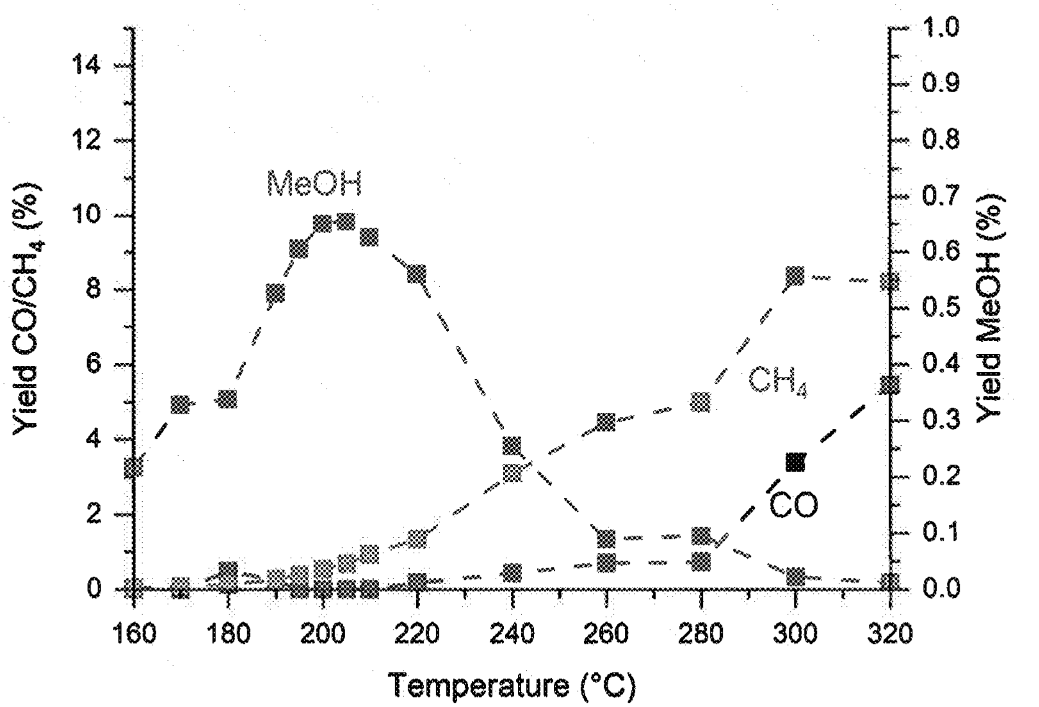
FIG. 1 shows the reaction yield of methanol from the reaction of $CO_2$ with $H_2$ over a $MoS_2$ catalyst promoted with manganese as a function of temperature in a process according to the invention.
Figure 2:
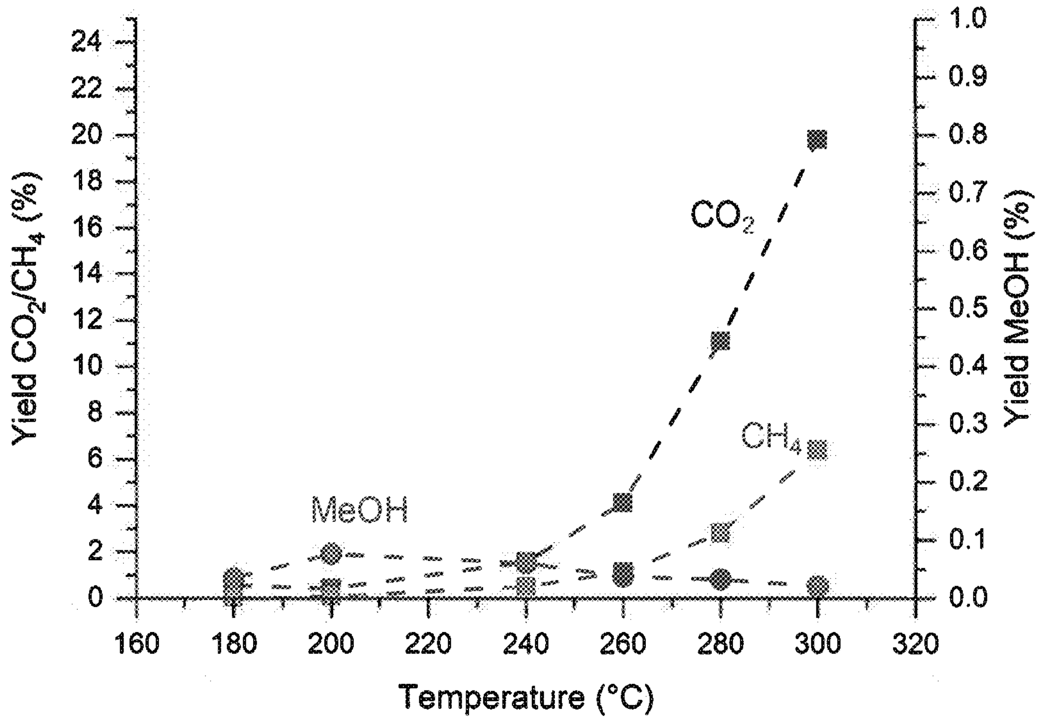
FIG. 2 shows the yield of the reaction of CO with $H_2$ over a $MoS_2$ catalyst promoted with manganese as a function of temperature.
Figure 3:
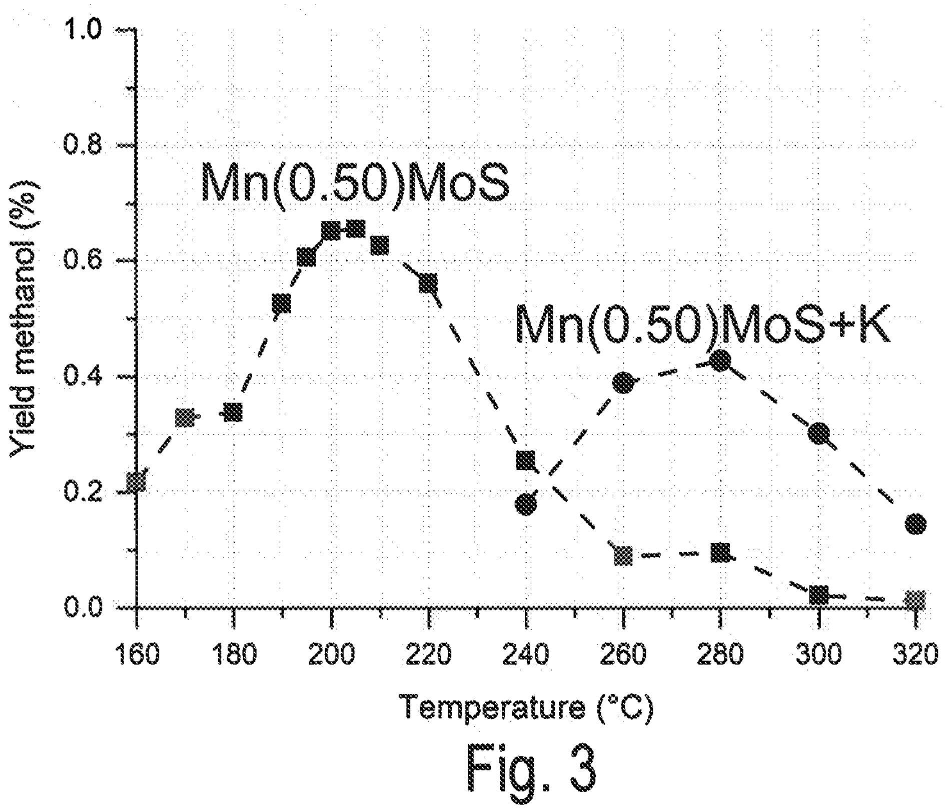
FIG. 3 shows the reaction yield of methanol from the reaction of $CO_2$ with $H_2$ as a function of temperature in a process according to the invention over a $MoS_2$ catalyst promoted with manganese without potassium (■) and with potassium (●).
Figure 4:
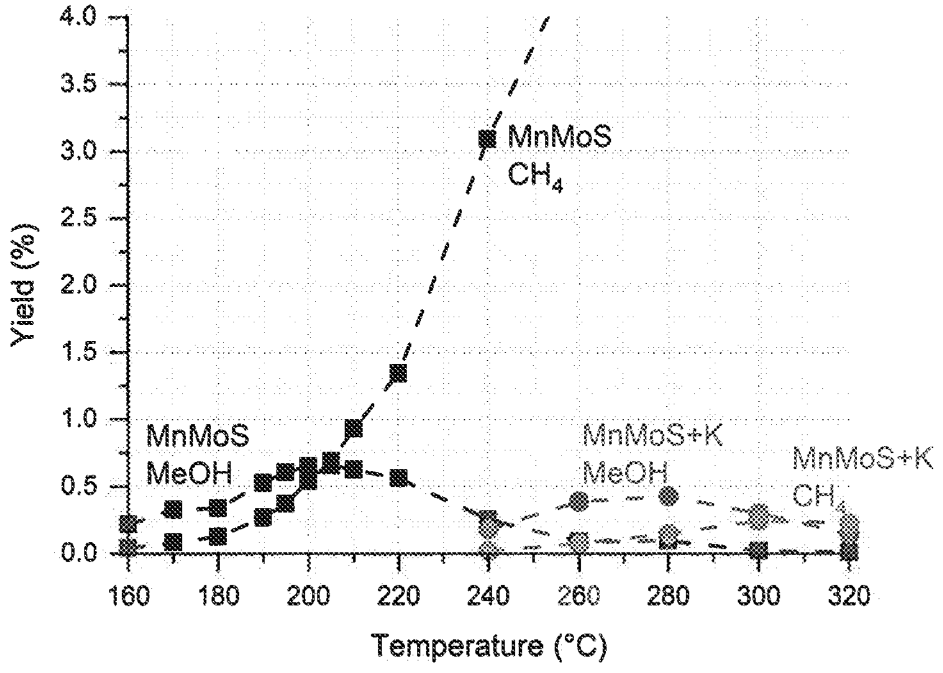
FIG. 4 shows a comparison of the reaction yields of methanol or, respectively, $CH_4$ from the reaction of $CO_2$ with $H_2$ as a function of temperature in a process according to the invention over a $MoS_2$ catalyst promoted with manganese without potassium (■) and with potassium (●).
Figure 5:
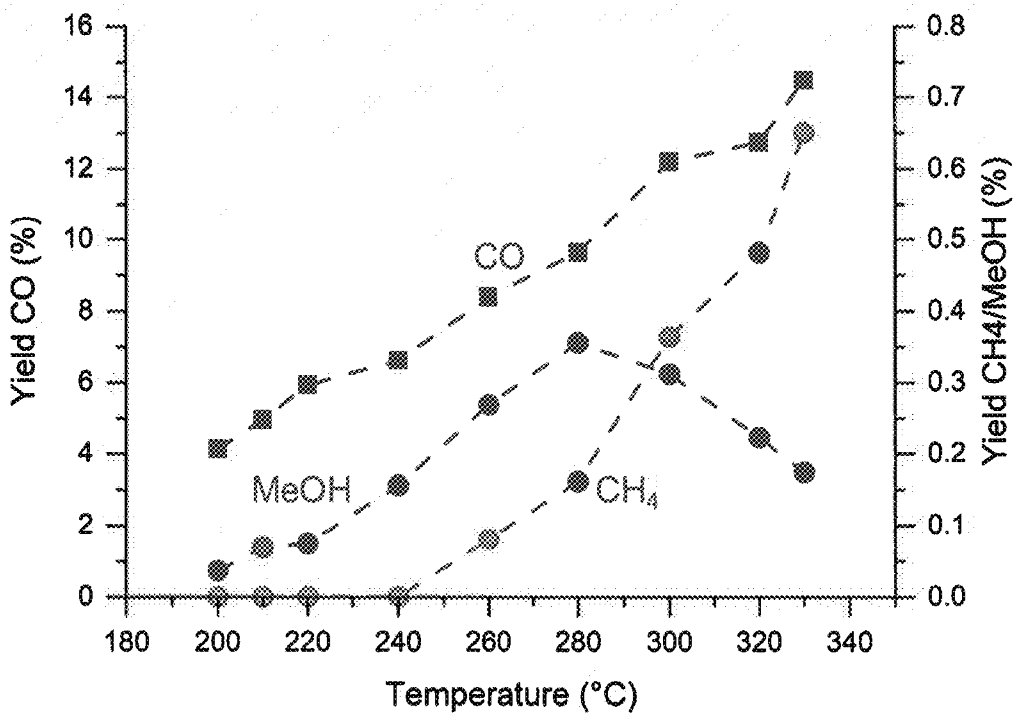
FIG. 5 shows the comparison of the reaction yield with a cobalt-promoted $MoS_2$ catalyst with potassium starting from $CO_2$ and $H_2$.
Figure 6:
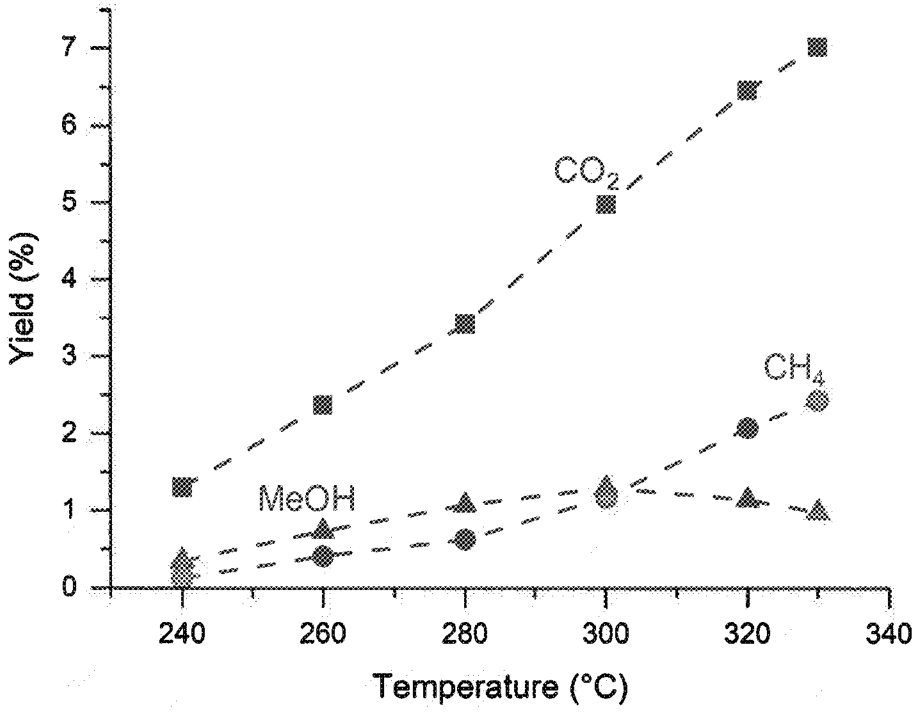
FIG. 6 shows the comparison of the reaction yield with a cobalt-promoted $MoS_2$ catalyst with potassium starting from CO and $H_2$.
Figure 7:
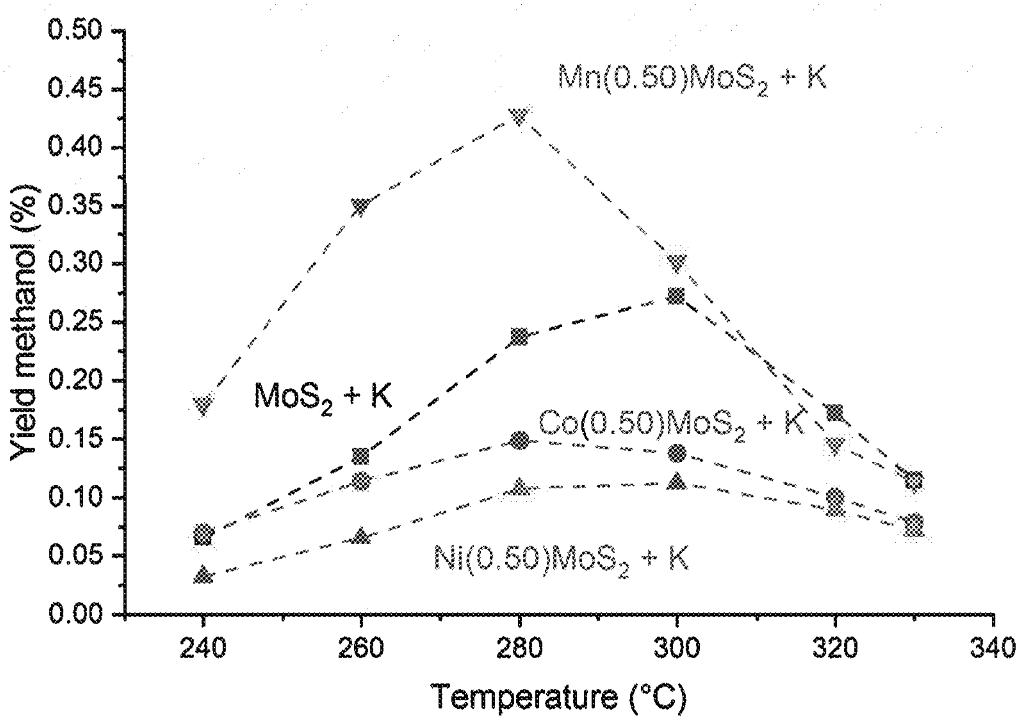
FIG. 7 shows different catalysts in the reaction of $CO_2$ with $H_2$ as a function of temperature.
Figure 8:
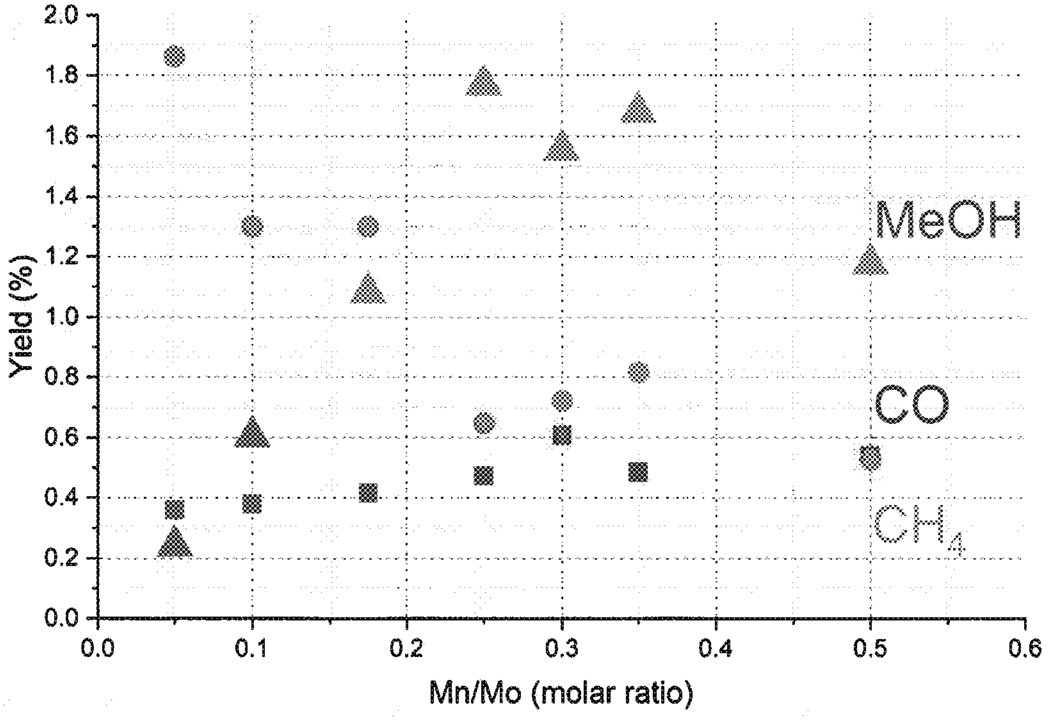
FIG. 8 shows a comparison of the reaction yields of methanol or, respectively, CO and $CH_4$ from the reaction of $CO_2$ with $H_2$ in a process according to the invention over various $MoS_2$ catalysts promoted with manganese with different proportions of Mn and Mo.
Figure 9:
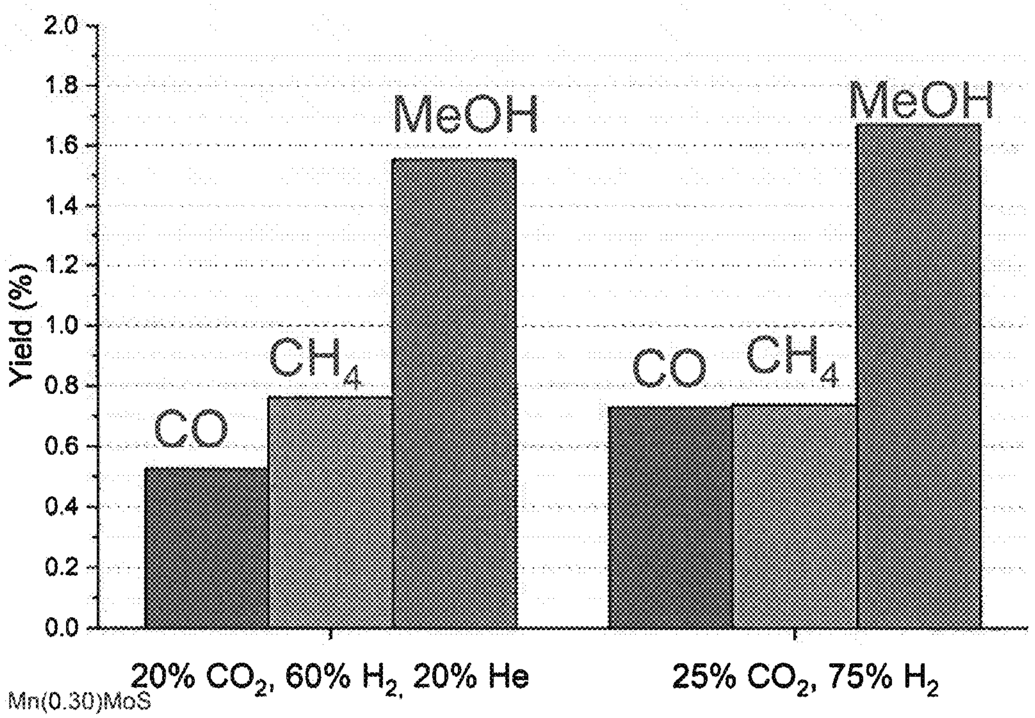
FIG. 9 shows a comparison of the reaction yields of methanol or, respectively, CO and $CH_4$ from the reaction of $CO_2$ with $H_2$ over a Mn(0.30)$MoS_2$ catalyst in the presence of 20% helium (on the left) and without helium (on the right).
Figure 10:
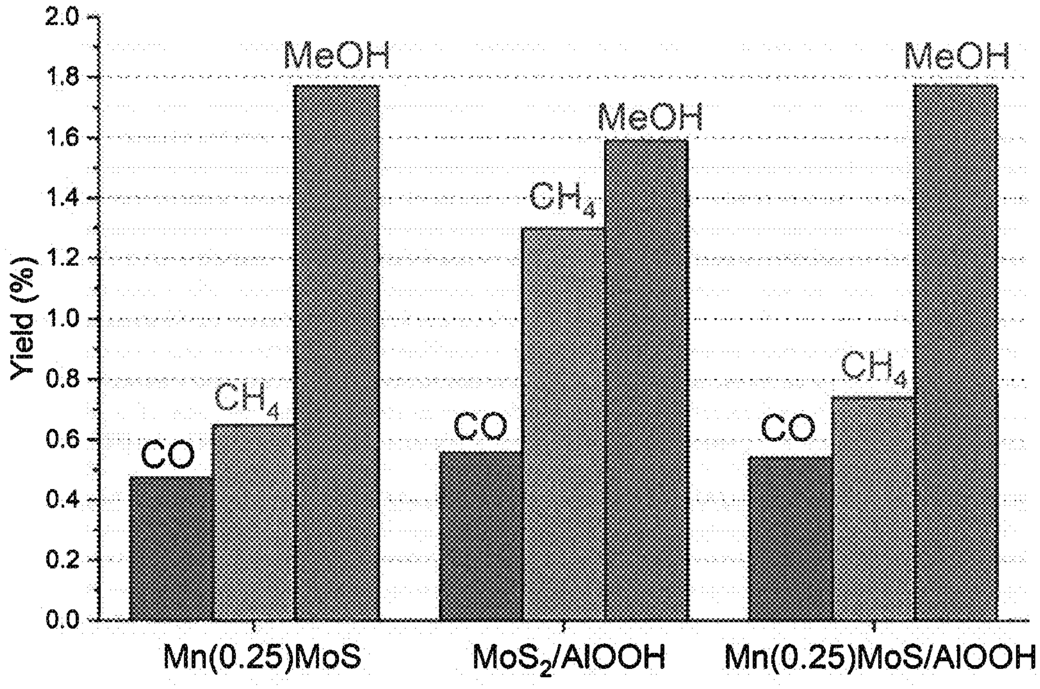
FIG. 10 shows a comparison of the reaction yields of methanol or, respectively, CO and $CH_4$ from the reaction of $CO_2$ with $H_2$ over a Mn(0.25)$MoS_2$ catalyst without a carrier (on the left), a $MoS_2$ catalyst with an AlO(OH) carrier (in the middle) and a Mn(0.25)$MoS_2$ catalyst with an AlO(OH) carrier (on the right).
Figure 11:
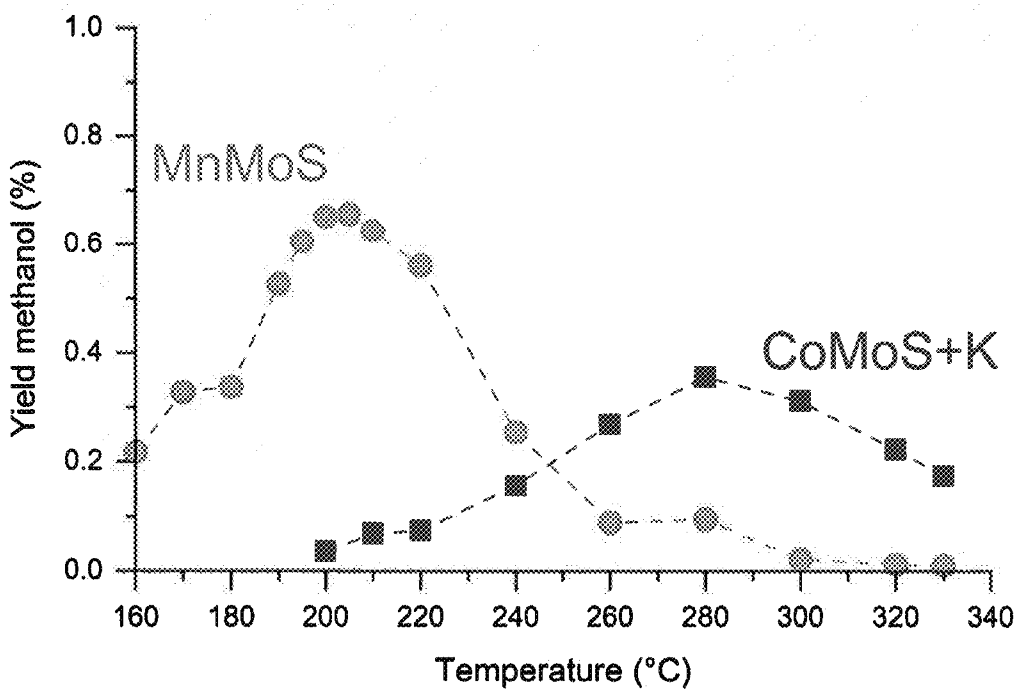
FIG. 11 shows a comparison of the reaction yields of methanol from the reaction of $CO_2$ with $H_2$ as a function of temperature over a $MnMoS_2$ catalyst and a cobalt-promoted $MoS_2$ catalyst.
Figure 12:
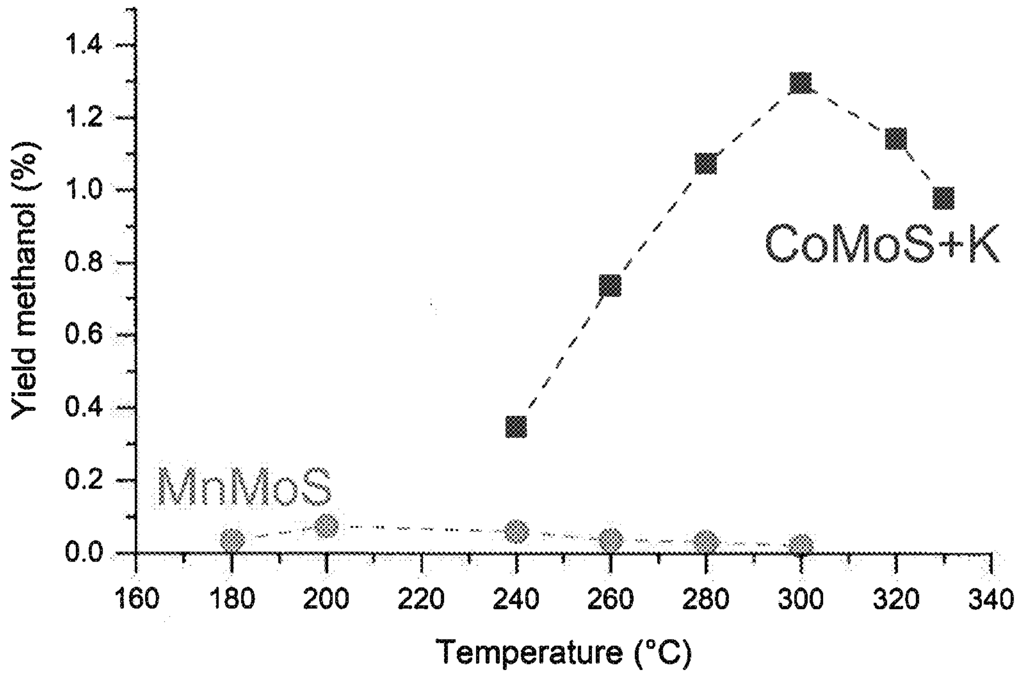
FIG. 12 shows a comparison of the reaction yields of methanol from the reaction of CO with $H_2$ as a function of temperature over a $MnMoS_2$ catalyst and a cobalt-promoted $MoS_2$ catalyst.

| FIG. | Total pressure | Partial pressure $CO_2$ | Partial pressure CO | Partial pressure $H_2$ | Partial pressure He |
|---|---|---|---|---|---|
| FIG. 1 | 21 bar | 20% | 0 | 60% | 20% |
| FIG. 2 | 21 bar | 0% | 20% | 60% | 20% |
| FIG. 3 | 21 bar | 20% | 0 | 60% | 20% |
| FIG. 4 | 21 bar | 20% | 0 | 60% | 20% |
| FIG. 5 | 21 bar | 20% | 0 | 60% | 20% |
| FIG. 6 | 21 bar | 0% | 20% | 60% | 20% |
| FIG. 7 | 21 bar | 20% | 0 | 60% | 20% |
| FIG. 8 | 21 bar | 20% | 0 | 60% | 20% |
| FIG. 9 | 21 bar | 20% | 0 | 60% | 20% |
| | 21 bar | 25% | 0 | 75% | 0% |
| FIG. 10 | 21 bar | 20% | 0 | 60% | 20% |
| FIG. 11 | 21 bar | 20% | 0 | 60% | 20% |
| FIG. 12 | 21 bar | 20% | 0 | 60% | 20% |

The total flow of the gas mixture as it is passed over the catalyst is:

$$\frac{300\text{ ml N}}{gkat * h}$$

In this formula, "ml N" stands for millilitres under normal or standard conditions, i.e., at 273.15 K or 0° C. and 1 bar pressure. The normalization to normal conditions is carried out because, under 21 bar, 1 ml would have a higher molar number than under 1 bar; therefore, the flow is converted and related to the volume flow under normal conditions.

In FIG. 1, the reaction yield of methanol as a function of temperature in a process according to the invention is shown, when $CO_2$ is allowed to react with $H_2$ over a simple molybdenum(IV) sulfide catalyst promoted with manganese. It can be seen very clearly that there is a maximum yield of methanol at around 200° C. to 210° C., while only a few by-products are formed at this temperature. With rising temperature, the formation of methane ($CH_4$) increases, while the yield of methanol decreases. The amount of carbon monoxide (CO) formed also increases with rising temperature. The ideal temperature range is therefore around 180° C. to 220° C.

FIG. 2 shows, in comparison to the example of FIG. 1, that the reaction yield of methanol as a function of temperature is extremely low in a process in which CO is allowed to react with $H_2$ over a molybdenum(IV) sulfide catalyst promoted with manganese. As the temperature rises, the formation of $CO_2$ and $CH_4$ begins. CO should therefore be irrelevant during the formation of methanol on said catalyst.

In FIG. 3, the reaction yields of the reaction $CO_2 + 2H_2 \rightarrow CH_3OH$ over a simple $MoS_2$ catalyst promoted with manganese (■; see example of FIG. 1) and over a $MoS_2$ catalyst promoted with manganese further with potassium (●) as a function of temperature in the process according to the invention are compared. As already described in FIG. 1, in case of simple manganese-promoted molybdenum(IV) sulfide, the reaction processes show a maximum yield at around 200 to 210° C. In case of the manganese-promoted $MoS_2$ catalyst with potassium, the maximum yield shifts to around 280° C. The addition of potassium therefore shifts the maximum yield towards higher temperatures, while a reduction in the yield (mol % based on the $CO_2$ used) from just under 0.7% to approx. 0.4% can be observed at the same time. However, the disadvantage resulting from the use of the manganese-promoted $MoS_2$ catalyst with potassium in the form of a lower yield combined with a higher ideal temperature range is accompanied by the advantage of a significant decrease in the formation of $CH_4$, with $CH_4$ being an undesirable by-product. This correlation is also illustrated in FIG. 4, where it is evident in this chart that, in case of simple (i.e., potassium-free) manganese-promoted molybdenum(IV) sulfide, the maximum yield of $CH_3OH$ is already associated with a significant increase in the yield of $CH_4$ at approx. 200 to 210° C. In case of the manganese-promoted $MoS_2$ catalyst with potassium, the methane yield is still low at the maximum yield for $CH_3OH$ at 280° C.

FIG. 5 shows the reaction yield of the reaction $CO_2 + 2H_2 \rightarrow CH_3OH$ as a function of temperature in a process over a $MoS_2$ catalyst promoted with cobalt. The maximum yield occurs at around 280° C. It is not difficult to see that, in comparison to $MoS_2$ catalysts promoted with manganese (with and without potassium), not only is the amount of $CH_4$ formed comparatively high, but especially also the amount of CO formed is so high that this catalyst is mostly unselective for the formation of methanol. The yield of CO is higher by orders of magnitude than that of methanol already at approx. 200° C., and the yield of $CH_4$ also increases significantly from around 280° C.

FIG. 6 shows, in comparison to the example of FIG. 5, the reaction yield of methanol as a function of temperature in a process in which CO reacts with $H_2$ over a cobalt-promoted $MoS_2$ catalyst with potassium. The yields of methanol and methane are slightly higher overall, but $CO_2$ is the main product even at low temperatures and from about 300° C. the $CH_4$ yield exceeds the amount of $CH_3OH$ formed.

FIG. 7 shows a comparison of the yield of methanol formed in the reaction of $CO_2$ with $H_2$ over various catalysts. A nickel-promoted $MoS_2$ catalyst with potassium (▲) provides the lowest yields. A $MoS_2$ catalyst promoted with cobalt shows only a slightly higher methanol yield (●). A $MoS_2$ catalyst with K (■) shows significantly better yields, but the highest yields can be found in the process according to the invention with manganese-promoted $MoS_2$ with potassium (▼).

The chart of FIG. 8 shows the comparison of the reaction yields of methanol (MeOH) or, respectively, CO and $CH_4$ from the reaction of $CO_2$ with $H_2$ in a process according to the invention over various manganese-promoted $MoS_2$ catalysts with different proportions of Mn and Mo. The abscissa shows the molar proportion of manganese in relation to molybdenum. The maximum methanol yield is from 0.2 to 0.4. (Reaction conditions: 21 bar, 180° C., 20% $CO_2$, 60% $H_2$, 20% He, 300 mlN/($g_{catalyst}$*h)

The column chart of FIG. 9 illustrates the reaction yields of methanol, $CH_4$ and CO from the reaction of $CO_2$ with $H_2$ over a Mn(0.30)$MoS_2$ catalyst in the presence and absence of helium as an inert gas. The yields of a mixture of 20% $CO_2$, 60% $H_2$ and 20% He are illustrated in the left-hand chart, a mixture of 25% $CO_2$ and 75% $H_2$ is illustrated in the right-hand chart. It can be seen that the yield of methanol decreases only slightly in the presence of He, surprisingly, the yield of CO decreases at the same time by a significant amount. (The reaction conditions are in each case 21 bar, 180° C., 300 mlN/($g_{catalyst}$*h)).

The column chart of FIG. 10 illustrates the reaction yields of methanol, $CH_4$ and CO from the reaction of $CO_2$ with $H_2$ over three different catalysts. The left-hand chart shows the yields over a manganese-promoted $MoS_2$ catalyst (Mn(0.25) $MoS_2$), the middle chart shows yields on a "simple" $MoS_2$ catalyst, and the right-hand chart shows those on a manganese-promoted $MoS_2$ catalyst (Mn(0.25)$MoS_2$) applied to an AlO(OH) carrier. A significantly higher selectivity of the two manganese-promoted $MoS_2$ catalysts with regard to methanol can be seen, the significantly lower yields of the undesired by-product $CH_4$ are particularly striking (reaction conditions: in each case 21 bar, 180° C., 20% $CO_2$ 60% $H_2$ 20%, He 300 mlN/($g_{catalyst}$*h))

FIG. 11 shows the comparison of the reaction yields of methanol of a manganese-promoted $MoS_2$ catalyst and a cobalt-promoted $MoS_2$ catalyst with potassium from the reaction of $CO_2$ with $H_2$ as a function of temperature. The reaction yields with the manganese-promoted $MoS_2$ catalyst are not only higher, but also shifted toward lower temperatures. (Reaction conditions: in each case 21 bar, 180° C., 20% $CO_2$ 60% $H_2$ 20% He, 300 mlN/($g_{catalyst}$*h).

Furthermore, FIG. 12 shows the comparison of the reaction yields of methanol of a manganese-promoted $MoS_2$ catalyst and a cobalt-promoted $MoS_2$ catalyst with potassium from the reaction of CO with $H_2$ as a function of temperature. In this depiction, the selectivity of the manganese-promoted $MoS_2$ catalyst can be seen even more clearly. (Reaction conditions: in each case 21 bar, 180° C., 20% CO 60% $H_2$ 20% He, 300 mlN/(($g_{catalyst}$*h). Since flue gas can comprise residual amounts of CO, the high selectivity which occurs when flue gas is used as a source for $CO_2$ constitutes an advantage over other catalysts.

In contrast to the prior art of sulfur-insensitive catalysts, the selective formation of methanol by means of $CO_2$ hydrogenation on a manganese-promoted $MoS_2$ (with or without potassium) catalyst is therefore significantly greater.

The invention claimed is:

1. A method for producing methanol ($CH_3OH$) from carbon dioxide ($CO_2$) and hydrogen ($H_2$), comprising reacting $CO_2$ with $H_2$ over a manganese-promoted molybdenum (IV) sulfide catalyst, wherein the manganese is present in an oxidation state of (II) or (III) or in oxidation states of both (II) and (III).

2. The method according to claim 1, wherein the reaction takes place at a pressure of ≥10 bar.

3. The method according to claim 1, characterized in that the partial pressure ratio of $CO_2$ to $H_2$ is about 1:2.5 to 1:3.5.

4. The method according to claim 1, wherein while $CO_2$ is reacted with $H_2$ over the manganese-promoted molybdenum(IV) sulfide, an inert gas is additionally present.

5. The method according claim 1, wherein the manganese-promoted molybdenum(IV) sulfide catalyst has a composition Mn(0.1 to 0.50) $MOS_2$, wherein the molar ratio of Mn to Mo is 0.1 to 0.5:1.

6. The method according to claim 1, wherein the reaction takes place at a temperature between 160° C. and 240° C.

7. The method according to claim 1, wherein the $CO_2$ source is flue gas.

8. The method according to claim 3, wherein the partial pressure ratio of $CO_2$ to $H_2$ is about 3.

9. The method according to claim 1, wherein manganese is present in both oxidation states of (II) and (III).

* * * * *